United States Patent [19]

Mita et al.

[11] Patent Number: 4,745,210
[45] Date of Patent: May 17, 1988

[54] PREPARATION PROCESS OF N-FORMYL-α-ASPARTYL PHENYLALANINE

[75] Inventors: Ryuichi Mita; Toshio Katoh, both of Kawasaki; Chojiro Higuchi, Kamakura; Takeshi Oura, Zushi; Akihiro Yamaguchi, Kamakura, all of Japan

[73] Assignee: Mitsui Toatsu Chemicals, Incorporated, Tokyo, Japan

[21] Appl. No.: 804,479

[22] Filed: Dec. 4, 1985

[30] Foreign Application Priority Data

Dec. 17, 1984 [JP] Japan ................. 59-264618

[51] Int. Cl.[4] .................. C07C 103/52; C07C 102/00
[52] U.S. Cl. ..................................... 560/41; 426/548; 560/40
[58] Field of Search ............... 260/998.21; 426/548; 548/478; 549/477; 560/40, 41

[56] References Cited

U.S. PATENT DOCUMENTS

| | | | |
|---|---|---|---|
| 3,879,372 | 4/1975 | Boesten | 560/41 |
| 3,933,781 | 1/1976 | Bachman et al. | 560/40 |
| 4,021,418 | 5/1977 | Takemoto et al. | 560/41 |
| 4,071,511 | 1/1978 | Takemoto et al. | 560/41 |
| 4,153,737 | 5/1979 | Berg et al. | 426/548 |

FOREIGN PATENT DOCUMENTS

| | | |
|---|---|---|
| 0092933 | 11/1983 | European Pat. Off. |
| 0127411 | 12/1984 | European Pat. Off. |
| 1370 | 7/1971 | Japan. |
| 96557 | 6/1973 | Japan. |
| 113841 | 4/1976 | Japan. |
| 40069 | 9/1976 | Japan. |
| 82752 | 3/1978 | Japan. |
| 219258 | 5/1984 | Japan. |
| 225153 | 5/1984 | Japan. |
| 225152 | 5/1984 | Japan. |
| 130846 | 10/1984 | Japan. |
| 1464140 | 2/1977 | United Kingdom. |
| 2133409 | 7/1984 | United Kingdom. |

*Primary Examiner*—Delbert R. Phillips
*Assistant Examiner*—Nathan M. Nutter
*Attorney, Agent, or Firm*—Fisher, Christen & Sabol

[57] ABSTRACT

This invention relates to an improved process for preparing N-formyl-α- aspartyl phenylalanine. More specifically, it relates to a process for preparing N-formyl-α-aspartyl phenylalanine by condensating N-formyl aspartic acid anhydride and phenylalanine which comprises effecting the condensation reaction in a water medium while maintaining the pH during the reaction in the range of 7–12 and at a reaction temperature of 50° C. or below.

3 Claims, No Drawings

PREPARATION PROCESS OF N-FORMYL-α-ASPARTYL PHENYLALANINE

BACKGROUND OF THE INVENTION

There has recently been a rapid increase in demand for α-L-aspartyl-L-phenylalanine methyl ester (Aspartame), an artificial dipeptide sweetening agent. N-formyl-α-aspartyl phenylalanine is an important compound as an intermediate for the preparation of Aspartame. Specifically, Aspartame can be prepared by deformylating N-formyl-α-aspartyl phenylalanine in a methanol-hydrochloric acid solution, followed by esterification (Japanese Patent Publication No. 26133/1980 and Japanese Patent Laid-Open No. 82752/1978).

Only Japanese Patent Publication No. 26133/1980 discloses a process for preparing N-formyl-α-aspartyl phenylalanine by condensating N-formyl aspartic acid anhydride and phenylalanine. This process comprises condensating N-formyl aspartic acid anhydride with phenylalanine in glacial acetic acid and, more specifically, comprises effecting the condensation reaction at 45°–50° C. by adding L-phenylalanine little by little to a mixture having N-formyl aspartic acid anhydride suspended in glacial acetic acid present in an amount ten times as great as the N-formyl aspartic acid anhydride.

In the condensation of N-formyl aspartic acid anhydride and phenylalanine, N-formyl-β-aspartyl phenylalanine (β-isomer), a product of the condensation of phenylalanine with β-carboxylic acid of aspartic acid, is simultaneously formed in addition to the intended N-formyl-α-aspartyl phenylalanine (α-isomer). However, only the ester derived from the α-isomer is useful as a sweetening agent while the ester derived from the β-isomer is an unfavorable substance since it has no sweetening effect but on the contrary exhibits a bitter taste.

In accordance with the disclosure of the above-described prior art, the condensation reaction of N-formyl aspartic acid anhydride and phenylalanine by-produces the β-isomer in such amounts of 20% or more. Accordingly, in order to produce the sweetening agent Aspartame at low cost on an industrial scale, it is necessary to re-utilize the β-isomer by separating it from the α-isomer and hydrolyzing it into aspartic acid and phenylalanine for reuse as a raw material.

However, in the process disclosed in Japanese Patent Publication No. 26133/1980 wherein the condensation reaction is practiced in acetic acid, it is necessary to treat the solvent acetic acid, for example, by removing it from the filtrate containing primarily the β-isomer, which has been separated with the α-isomer after the reaction, prior to the recovery of aspartic acid and phenylalanine from the β-isomer by hydrolysis. In other words, the prior art process has the disadvantages of involving complicated procedures.

SUMMARY OF THE INVENTION

An object of the present invention is to solve the disadvantages of the prior art process, i.e., the disadvantages encountered upon the treatment of the by-produced β-isomer in the condensation technique of N-formyl aspartic acid anhydride and phenylalanine in acetic acid solvent, and thereby to provide a more efficient process for the condensation reaction. This object can be achieved by carrying out the condensation reaction efficiently by the proper selection of the reaction conditions and reaction method even in a water medium without using any organic solvent. According to the process of the present invention, the α-isomer is formed in an overwhelmingly large amount and only a small amount of the β-isomer is formed in the condensation reaction. Further, upon the isolation of the intended product, only the intended α-isomer or a mixture of the α-isomer and the β-isomer can be separated by selecting the acidifying conditions properly.

Thus, the overall yield of the mixture of the α-isomer and the β-isomer is as high as 95% or more in spite of the fact that the condensation reaction is practiced in water. The ratio of the isomers formed is approximately α:β=8:2, indicating that the intended α-isomer is formed in an overwhelmingly large amount which may favorably be compared with that of the acetic acid solvent process. Moreover, the acidification of the reaction solution with hydrochloric acid or the like in a selected pH range after the reaction permits the selective isolation of the α-isomer containing almost no β-isomer, resulting in an extremely high rate of recovery of the intended product.

On the other hand, the β-isomer is transferred to the filtrate which has been separated with the α-isomer as crystals. Since the solvent is water, it is only necessary to subject the filtrate to hydrolysis by heating it in the presence of hydrochloric acid or the like and, after its concentration as required, to crystallization of aspartic acid and phenylalanine at their respective isoelectric points. Thus, the complexity of the recovery process accompanied by the condensation reaction in acetic acid medium as described above is advantageously eliminated.

DETAILED DESCRIPTION OF THE INVENTION

The present invention provides a process for preparing N-formyl-α-aspartyl phenylalanine by condensating N-formyl aspartic acid anhydride and phenylalanine which comprises effecting the condensation reaction in a water medium while maintaining the pH during the reaction in the range of 7–12 and at a reaction temperature of 50° C. or below.

The process of the present invention employs N-formyl aspartic acid anhydride as a raw material. The starting N-formyl aspartic acid anhydride can be readily prepared, for example, by treating aspartic acid with formic acid and acetic anhydride. Although no particular limitations are imposed on the amount of N-formyl aspartic acid anhydride to be used, it may generally be used in stoichiometrical excess of phenylalanine. However, it is not necessary to use it in unduly excessive amounts.

There are no particular limitations on the amount of water to be used as a solvent in the process of the present invention. It may be used in an amount by weight 3–50 times or generally 5–30 times that of phenylalanine in view of the reaction operation and the volume efficiency.

There is no particular limitation on the mode of the reaction so long as it is capable of preventing the ring-opening reaction of N-formyl aspartic acid anhydride by water to the greatest possible extent and of allowing N-formyl aspartic acid anhydride and phenylalanine to react with each other at a pH in the range of 7–12. For example, one mode is to feed N-formyl- aspartic acid anhydride little by little continuously or dividedly into a solution or suspension prepared by introducing phenylalanine and an alkali into water. In this mode, the pH of the reaction liquid is adjusted by adding dropwise an aqueous alkaline solution so that it is kept in the range of 7–12. In this case, as the alkali for use in dissolving phenylalanine in the initial stage and in adjusting pH during the reaction, there may suitably be used the hydroxides, oxides or carbonates of alkali metals such as lithium, sodium and potassium and the hydroxides, oxides or carbonates of alkaline earth metals such as calcium and magnesium. As a matter of course, no problems or difficulties will be raised even if organic bases represented by triethylamine which is inactive to the anhydride are used. Under strongly alkaline conditions in which the pH of the reaction liquid exceeds 12, the ring-opening reaction of N-formyl aspartic acid anhydride by water is accelerated, thereby consuming an increased amount of N-formyl aspartic acid anhydride and at the same time unfavorably forming other by-products than the $\beta$-isomer. Further, an excessively acidic-sided pH during the reaction will cause the condensation reaction to retard unfavorably and the ring-opening reaction of the anhydride by water to take place preferentially. The reaction temperature is 50° C. or below, preferably 30° C. or below or more preferably 20° C. or below, for the purpose of preventing the hydrolysis of N-formyl aspartic acid anhydride by water. Although no particular restrictions are placed on its lower limit, it is advantageous to carry out the reaction at a temperature above $-20°$ C. from the industrial standpoint.

In the process of the present invention, there is no inconvenience to use jointly organic solvents which are missible with water, for example, lower alcohols such as methanol, ethanol, n-propanol, i-propanol, n-butanol and tert-butanol, and ether series solvents such as dioxane and tetrahydrofuran.

Thus, N-formyl-$\alpha$-aspartyl phenylalanine is formed by the reaction of N-formyl aspartic acid anhydride with phenylalanine. However, as mentioned above, its isomer, N-formyl-$\beta$-aspartyl phenylalanine is partly by-produced. The ratio of formation of the $\alpha$-isomer to the $\beta$-isomer is approximately in the range of 75:25–80:20, and the overall yield of the intended product and the $\beta$-isomer is 95% or more.

In the process of the present invention, the intended reaction product is in the state of solution after completion of the reaction. To isolate the intended product, the reaction solution is acidified by the addition of a mineral acid such as hydrochloric acid or sulfuric acid, thereby causing the intended product to precipitate, followed by filtration of the thus-precipitated crystals. In this case, only the $\alpha$-isomer is virtually selectively precipitated by adjusting the pH of the solution to 2.5–3.5. Accordingly, N-formyl-$\alpha$-aspartyl phenylalanine can be obtained in a high yield by cooling and aging the liquid-solid mixture resulting from the acidification and by separating the solid from the liquid. In this instance, the $\beta$-isomer is largely contained in the filtrate so that it can be re-utilized by hydrolyzing it, for example, with hydrochloric acid into aspartic acid and phenylalanine for use as a raw material.

On the other hand, if the pH is reduced to 2.5 or lower during the acidification, the resulting N-formyl-$\alpha$-aspartyl phenylalanine is admixed with a gradually increasing amount of the $\beta$-isomer. For example, at pH=1, a mixture containing about 20% of the $\beta$-isomer is isolated.

The present invention will hereinafter be described with reference to Examples and Comparative Examples. The analytical conditions of high speed liquid chromatography employed in the Examples and Comparative Examples are as follows:

Column: YMC Pack A-312 (ODS) 6 mm$\phi \times$150 mm
Moving phase: 0.001M $KH_2PO_4$aq:MeOH=8:2 (volume ratio) pH =2.3
Flow rate: 1.3 ml/min
Sensor: ultraviolet spectrometer wave length=225 nm

EXAMPLE 1

To an aqueous solution containing 13.2 g of potassium hydroxide dissolved in 330 ml of water was added 33.0 g (0.20 mole) of L-phenylalanine to form a solution. After being cooled to $-5°$ C., the solution was fed little by little with 30.0 g (0.21 mole) of N-formyl-L-aspartic acid anhydride for one hour while maintaining its temperature at $-5°$ C. to 5° C. A 10% aqueous sodium hydroxide solution was added thereto simultaneously to maintain the reaction liquid at a pH of 8–11. Thereafter, the reaction was carried out at the same temperature for one hour. The reaction mixture was analyzed by high speed liquid chromatography, with the result that the isomer formation ratio of N-formyl-$\alpha$-L-aspartyl-L-phenylalanine to N-formyl-$\beta$-L-aspartyl-L-phenylalanine was 78:22 while the overall yield was 98% based on L-phenylalanine.

Conc. hydrochloric acid was added dropwise to the reaction liquid at a temperature of 10° C. or below until its pH reached 3, and the resulting liquid mixture was stirred at 0°–5° C. for one hour. The precipitate thereby obtained was filtered, washed with cold water and dried to obtain 44.9 g of a white crystal of N-formyl-$\alpha$-L-aspartyl-L-phenylalanine in a yield of 72.9%.

The crystal was analyzed by high speed liquid chromatography, with the result that 2.0% of the $\beta$-isomer was admixed and the N-formyl-$\alpha$-L-aspartyl-L-phenylalanine had a purity of 97.8%.

COMPARATIVE EXAMPLE 1

To 330 ml of water was added 33.0 g (0.20 mole) of L-phenylalanine and the resulting suspension was cooled to 0° C. To the suspension was added little by little 30.0 g (0.21 mole) of N-formyl-L-aspartic acid anhydride at 0°–5° C. for about one hour. Thereafter, the reaction was effected at the same temperature for two hours. Then, a portion of the reaction mixture was analyzed by high speed liquid chromatography. As a result, it was observed that almost no N-formyl-$\alpha$-L-aspartyl-L-phenylalanine was formed.

COMPARATIVE EXAMPLE 2

To an aqueous solution containing 14.5 g of potassium hydroxide dissolved in 330 ml of water was added 33.0 g (0.20 mole) of L-phenylalanine to form a solution. After being cooled to a temperature of from 0° to $-5°$ C., 31.5 g (0.22 mole) of N-formyl-L-aspartic acid anhydride was added little by little to the solution for one hour while the temperature at 0°–5° C. was maintained. A 10% aqueous sodium hydroxide solution was simultaneously added thereto dropwise to maintain the reaction liquid at a pH of 12–14. Thereafter, the reaction was continued at the same temperature for one hour. A portion of the reaction mixture was subjected to high speed liquid chromatography for analysis. As a result, it was found that the isomer formation ratio of N-formyl-$\alpha$-L-aspartyl-L-phenylalanine to N-formyl-$\beta$-L-aspartyl-L-phenylalanine was 78:22, the same as in Example 1, while the overall yield was 80.4% based on L- phenylalanine, and 10.5% of the starting L-phenylalanine remained. Further, it was observed that about 10% of impurities were by-produced and the reaction liquid was extremely yellowish.

EXAMPLES 2-5 washed with cold water and then dried in vacuo to obtain 58.6 g of a crystal in a yield of 95.1%.

The crystal was analyzed by high speed liquid chromatography, with the result that the ratio of N-formyl-α-L-aspartyl-L-phenylalanine to N-formyl-β-L-aspartyl-L-phenylalanine was 78:22.

TABLE 1

| Example No. | Initial amount of water (ml) | Alkali | Reaction temperature (°C.) | pH | Reaction liquid analysis (mole %/L-phenylalanine) N—formyl-α-L-aspartyl-L-phenylalanine | N—formyl-β-L-aspartyl-L-phenylalanine | Isolation yield of N—formyl-α-L-aspartyl-L-phenylalanine (%/L-phenylalanine) |
|---|---|---|---|---|---|---|---|
| 2 | 330 | 10% NaOH | 5-10 | 8-10 | 74.6 | 22.5 | 68.4 (purity 97.1%) |
| 3 | 230 | 10% NaOH | 0-5 | 8-10 | 74.1 | 20.9 | 67.5 (96.4%) |
| 4 | 330 | 10% LiOH | 0-5 | 8-10 | 76.3 | 22.8 | 69.4 (98.3%) |
| 5 | 330 | 20% $K_2CO_3$ | 0-5 | 7.5-9.5 | 76.0 | 22.5 | 70.2 (97.6%) |

The reaction was effected using 33.0 g (0.20 mole) of L-phenylalanine and 31.5 g (0.22 mole) of N-formyl-L-aspartic acid anhydride in the same manner as described in Example 1 except that the type of alkali, the reaction temperature, the pH and other conditions were changed as shown in Table 1. The results are summarized in Table 1.

EXAMPLE 6

Using 33.0 g (0.20 mole) of L-phenylalanine and 30.0 g (0.21 mole) of L-aspartic acid anhydride, the reaction was effected in the same manner as described in Example 1. After completion of the reaction, conc. hydrochloric acid was added dropwise to the reaction mixture until its pH reached 1 while the temperature was maintained at 10° C. or below. The resulting mixture was stirred at 0°-5° C. for one hour to cause a precipitate to deposit. The resulting precipitate was filtered,

What is claimed is:

1. Process for preparing N-formyl-α-aspartyl phenylalanine by condensating N-formyl aspartic acid anhydride and phenylalanine, comprising adding the N-formyl aspartic acid anhydride to the phenylalanine dissolved in an aqueous solution, the pH of the aqueous solution being maintained in the range of 7 to 12 by adding an aqueous alkaline solution, and the reaction temperature being maintained at 50° C. or below.

2. The process as claimed in claim 1 wherein, after the reaction is effected, the resultant reaction solution is adjusted to a pH in the range of 2.5 to 3.5 so that N-formyl-α-aspartyl phenylalanine can be precipitated and isolated.

3. The process as claimed in claim 1 wherein, after the reaction is effected, the resultant reaction solution is adjusted to a pH below 2.5 so that a mixture of N-formyl-α-aspartyl phenylalanine and N-formyl-β-aspartyl phenylalanine can be precipitated and isolated.

* * * * *